United States Patent
Kang

(10) Patent No.: US 11,872,622 B2
(45) Date of Patent: Jan. 16, 2024

(54) NITINOL NANOFIBERS

(71) Applicant: TINIKO CO., LTD., Cheongju-si (KR)

(72) Inventor: Ji-Hoon Kang, Cheongju-si (KR)

(73) Assignee: TINIKO CO., LTD., Cheongju-si (KR)

(*) Notice: Subject to any disclaimer, the term of this patent is extended or adjusted under 35 U.S.C. 154(b) by 0 days.

(21) Appl. No.: 18/017,027

(22) PCT Filed: Jul. 23, 2021

(86) PCT No.: PCT/KR2021/009536
§ 371 (c)(1),
(2) Date: Jan. 19, 2023

(87) PCT Pub. No.: WO2022/025532
PCT Pub. Date: Feb. 3, 2022

(65) Prior Publication Data
US 2023/0241673 A1 Aug. 3, 2023

(30) Foreign Application Priority Data

Jul. 28, 2020 (KR) .................. 10-2020-0093952

(51) Int. Cl.
| | | |
|---|---|---|
| B22F 1/054 | (2022.01) | |
| C22C 19/00 | (2006.01) | |
| B22F 1/16 | (2022.01) | |
| B22F 1/17 | (2022.01) | |
| A61L 31/14 | (2006.01) | |
| C22F 1/10 | (2006.01) | |

(52) U.S. Cl.
CPC ............ B22F 1/0547 (2022.01); A61L 31/14 (2013.01); B22F 1/16 (2022.01); B22F 1/17 (2022.01); C22C 19/007 (2013.01); C22F 1/10 (2013.01); A61L 2400/12 (2013.01); A61L 2400/18 (2013.01)

(58) Field of Classification Search
CPC .. B22F 2301/15; B22F 301/205; C22C 49/11; C22C 19/03; C22C 1/0433
See application file for complete search history.

(56) References Cited

U.S. PATENT DOCUMENTS

2007/0225795 A1* 9/2007 Granada ............... A61F 2/91
623/1.36

FOREIGN PATENT DOCUMENTS

| JP | 2000-297530 A | 10/2000 |
|---|---|---|
| JP | 2009-518082 A | 5/2009 |
| KR | 10-2012-0117169 A | 10/2012 |
| KR | 10-2013-0076438 A | 7/2013 |
| KR | 10-2017-0003449 A | 1/2017 |
| KR | 10-2017-0114805 A | 10/2017 |
| KR | 10-2019-0118307 A | 10/2019 |
| KR | 10-2020-0084942 A | 7/2020 |

OTHER PUBLICATIONS

Nasakina et al. Inorganic Materials: Applied Research, 2015, 6(1), 53-58.*
Shabalovskaya et al. Biomaterials, 30, 2009, 468-477.*
Johnson Matthey: Nitinol technical properties, 3 pgs.*
Wick et al., J de Physique, 5, 1995, 789-794.*
International Search Report for PCT/KR2021/009536 dated Oct. 19, 2021 [PCT/ISA/210].
Written Decision on Registration for KR 10-2020-0093952 dated Oct. 13, 2021.
Request for the Submission of an Opinion for KR 10-2020-0093952 dated Sep. 28, 2021.

* cited by examiner

*Primary Examiner* — Kyle A Purdy
(74) *Attorney, Agent, or Firm* — Sughrue Mion, PLLC

(57) ABSTRACT

Proposed is a nitinol nanofiber with an average surface roughness that is enhanced through mechanical and chemical treatments. The enhanced surface roughness improves biocompatibility and promotes tissue growing, thereby improving the bioavailability of the nitinol nanofiber. The nitinol nanofiber undergoes infrared irradiation whereby the nitinol fiber exhibits improved tensile strength, elastic modulus, and maximum restorative stress. Therefore, fatigue fraction does not easily occur in the nitinol fiber even when the nitinol nanofiber has a constant roughness. The present invention provides bio-use or medical nitinol nanofibers that are highly biocompatible.

10 Claims, No Drawings

NITINOL NANOFIBERS

CROSS REFERENCE TO RELATED APPLICATIONS

This application is a National Stage of International Application No. PCT/KR2021/009536 filed Jul. 23, 2021, claiming priority based on Korean Patent Application No. 10-2020-0093952 filed Jul. 28, 2020, the entire disclosures of which are incorporated herein by reference.

TECHNICAL FILED

The present invention relates to nitinol nanofibers. More particularly, the present invention relates to a new type of nitinol nanofibers made of an alloy of nickel and titanium and having surface roughness introduced during a manufacturing process whereby the nitinol nanofibers have physical properties suitable for used as biomaterials or medical materials.

BACKGROUND ART

Nitinol is an alloy of nickel and another metal. A nitinol material is known as a shape memory alloy (SMA), which memorizes a specific shape when exposed to a predetermined temperature after being manufactured into a molded product. After the nitinol material is deformed, it recovers its original specific shape.

In addition to the shape-memory property, nitinol is also known to have a superelastic property. When a substantial amount of transformation exceeding the plastic strain range occurs in the superelastic shape-memory alloy at room temperature, the superelastic shape-memory alloy returns to the original shape after removal of the load.

Nitinol, which has such excellent physical properties, is a material that can be applied to various materials due to the physical properties of superelastic shape memory alloy and can be used as a high-tech material to manufacture medical devices and other high-performance industrial devices.

Nitinol shape memory alloy, which is a general nickel-titanium alloy, is produced by mixing nickel and titanium to have the same distribution and is relatively widely used among shape memory alloy materials.

Nitinol shape memory alloy has a martensite phase that is relatively weak and an austenite phase that is relatively strong, depending on applied temperature and stress. At temperatures (T-Mf) below the martensite transformation temperature, only elastic recovery occurs after a relatively low stress plateau and load removal, but a significant amount of residual deformation actually occurs. When heating is additionally performed, phase transformation from martensite to austenite occurs, showing a shape memory effect (SME) leading to the nitinol material recovers the original shape.

On the other hand, at or above the austenite phase transformation temperature, even when a substantial amount of plastic strain is applied to the material, a superelastic behavior in which the material is restored to the original shape occurs even without additional heating. The superelastic shape memory alloy shows a flag-shaped hysteresis behavior composed of a total of 6 zones including an elastic behavior zone occurring within 1% of strain, a forward phase transformation zone in which phase transformation from austenite to martensite occurs in stress plateaus, a stress hardening zone due to re-elastic behavior, an unloading elastic strain recovery zone, a reverse phase transformation zone in which stress recovery occurs so that the phase returns to the austenite phase, and an elastic recovery zone with no residual deformation.

The shape-memory alloy in the austenite state has the property of being automatically restored to the original shape and of having negligible residual deformation after stress removal when a maximum of 8% strain is loaded even though no additional heating is performed. When the phase transformation temperature rises to above a certain temperature, the strength increases beyond the plateau zone caused by the slip of stress in the austenite state, and ordinary plastic deformation occurs at the time of unloading (Chong-Wan Ha et al., "Numerical Reproduction of Quasi-Static Behavior of Superelastic Nitinol Shape Memory Alloy", Journal of Korean Society of Steel Structures, Vol.27, No.6, pp.493-501, December 2015).

Nitinol materials are categorized into two types according to physical properties. Superelastic nitinol is generally known to be used in medical devices, and the transition temperature of the superelastic grade nitinol is in a range of −15° C. to 22° C.

Shape-memory nitinol is generally used in actuators and other industrial applications, and the transition temperature of the shape-memory grade nitinol is in a range of 22° C. to 80° C. Some grades of nitinol have transformation temperatures in a range of 85° C. or higher.

Nitinol with these properties is used as a biomedical material. For example, nitinol is utilized in various biomaterials. For example, there are many cases in which the nitinol is used as a stenting material (Korean Patent Application Publication No. 10-2020-0084942, etc.). In addition, the nitinol is used an implant material (U.S. Patent Publication No. 2014-0120544, etc.), a prosthesis material (Japanese Patent Registration No. 6557008, etc.), etc.

In addition, nitinol is used as an electronic material on semiconductor substrates or is used to manufacture highly functional industrial wires.

Among the nitinol materials used in biomaterials, there are cases in which nitinol is manufactured in the form of wires or fibers. Among them, a case in which nitinol is used to manufacture nanofibers which are applied to artificial ligaments is known (U.S. Pat. No. 7,905,918).

However, despite the excellent physical properties of nitinol materials as a superelastic shape memory alloy, it is necessary to develop various functional medical materials required for biological applications. In particular, it is necessary to develop nanofibers having physical properties suitable for materials applied to sites (for example, joints) where continuous relaxation and contraction are repeatedly performed.

For example, in the case of nanofibers being applied to artificial ligaments as disclosed in U.S. Pat. No. 7,905,918, since the nanofibers do not have sufficient cell adhesion and do not meet the physical properties that can be maintained without breaking for a sufficiently long period of time is not obtained, it is difficult to apply the nanofibers to as real products. For this reason, artificial ligaments utilize polymer fabrics rather than metal materials. However, the polymer materials can easily break during use and cause inflammation due to the irritation by sharp margins of the broken polymer material. Therefore, the polymer materials are not actively used.

As such, despite the excellent physical properties of nitinol materials, it is necessary to improve the physical properties such as durability when used as biofilms, and it is difficult to use nitinol materials as medical materials due to limitations in human applicability such as cell activity. Therefore, the physical properties of nitinol materials need to be improved.

Regarding a nitinol nanofiber production method, a conventional processing method is used when processing a wire having a diameter of 1 mm or more. However, it is difficult to use the conventional method when producing an ultra-fine wire having a diameter of 100 μm, which is thinner than 0.1 mm.

When ultra-fine wires are thermomechanically processed, the optimal processing conditions are required. That is, the uniform plastic deformation by mechanical working and the removal of residual stress by heating for subsequent working are required so that the entire ultra-fine wire can have uniform composition and physical properties. However, in the heat treatment rolling process of the current technology for producing a uniform ultra-fine wire, it is difficult to apply uniform temperature to the entire ultra-fine wire during the heat treatment process. Therefore, there are drawbacks such as breaking or heterogeneous physical properties.

In addition, even in a cold working process for nitinol, there are problems in that reduction in elastic force of an alloy causes higher friction resistance, and the product quality is lowered due to an increase in rotational contact. Therefore, a process for overcoming the problems is required.

DISCLOSURE

Technical Problem

In order to solve the problems of related arts, the present invention aims to develop a biomaterial with good surface roughness.

Accordingly, it is an objective of the present invention to provide a nitinol material having excellent tensile strength for biomedical applications.

Another objective of the present invention is to provide a nitinol nanofiber having good biocompatibility by ensuring formation of an oxide layer.

In addition, a further objective of the present invention is to provide a bio-use nitinol nanofiber with good bioavailability.

Technical Solution

In order to solve the above problems, the present invention provides a nitinol nanofiber made of a nitinol alloy, which is an alloy of nickel and titanium.

The present invention relates to new nitinol nanofibers having improved physical properties. Embodiments described below are presented only for illustrative purposes to describe the present invention, and thus the present invention is not limited thereto and can be embodied in various other embodiments.

The term "nitinol" as used herein means an alloy of nickel and titanium.

In one embodiment of the present invention, the nitinol nanofibers have a nanofiber shape having a maximum diameter of 10 nm to 1,000 nm and have a continuous or discontinuous surface roughness. The surface roughness has a regular or irregular form and is foamed in an area of 10% to 30% with respect to the entire surface. The average roughness $R_a$ is in a range of 0.5 nm to 40 nm, and a roughened region has a top-bottom height difference $R_{max}$ of 0.01 to 80 nm.

The nitinol nanofiber of the present invention has a region with surface roughness, thereby controlling the adsorption and proliferation rate and increasing the density of grown tissue.

When the largest diameter of the nitinol nanofiber is smaller than 10 nm, the elasticity of the nitinol nanofiber is insufficient. When the largest diameter is larger than 1000 nm, the elastic modulus decreases due to an increase in stiffness. Therefore, there is a problem in that it is difficult to use the nitinol nanofiber for artificial ligaments.

The nitinol nanofiber may have a roughness region. The roughness may be formed throughout the entire surface or only in some regions. When the roughness region accounts for less than 10% of the entire surface area, an effect of improving the degree of cell adhesion to the surface of the nitinol nanofiber surface is insignificant. When the roughness region accounts for more than 30%, fatigue fraction is likely to occur, thereby not being suitable for achieving the objectives of the present invention.

Fiber surface cell affinity is not enhanced when the average roughness is less than 0.5 nm $R_a$. When the average roughness exceeds 40 nm $R_a$, the likelihood of fatigue fraction increases, thereby not being suitable for achieving the objectives of the present invention.

When a height difference between the top and bottom of a roughened region is less than 0.01 nm, the roughness of the roughened region is insufficient. When the height difference exceeds 80 nm, due to deep troughs and crests, the degree of cell adhesion is reduced, thereby not being suitable for achieving the objectives of the present invention.

In one embodiment of the present invention, the nitinol nanofiber further has one or more properties selected from among a density of 4 to 9 g/cm$^3$, an elastic modulus of 20 to 120 GPa, a maximum recovery rate of 100%/1 million cycles, a maximum recovery stress of 800 MPa, a thermal expansion modulus of $6.6 \times 10^{-6}$ to $11 \times 10^{-6}$/° C.

When the density is lower than 4 g/cm$^3$, the fiber strength is low. When the density is higher than 9 g/cm$^3$, the fiber bundle weight is large, thereby being unsuitable for achieving the objectives of the present invention.

When the elastic modulus falls outside the range of 20 to 120 Gpa, the force required for fiber elongation-restoration is excessively weak or strong.

When the maximal recovery rate is less than 100%/1 million cycles, there is a problem with poor long-term prognosis after artificial ligament reconstruction surgery.

When the maximum recovery stress is less than 800 MPa, when an excessive force is applied momentarily, the artificial ligament remains stretched and needs to be replaced.

In one embodiment of the present invention, the nitinol nanofiber may have a tensile strength in a range of 1000 to 2000 MPa.

When the tensile strength is less than 1000 MPa, the nitinol fiber cannot withstand a momentary excessive force and thus breaks. Conversely, when the tensile strength is greater than 2000 MPa, such a high strength can be obtained when the nitinol nanofiber has a diameter larger than 1000 nm.

In one embodiment of the present invention, the nitinol nanofiber may contain 40% to 50% by weight of titanium, 50% to 60% by weight of nickel, and 0% to 10% by weight of one or more elements selected from the group consisting of Mo, Fe, Al, C, N, and O.

When the content of each component in the alloy composition is outside the range described above, there may a problem in that a stable phase transformation between martensite and austenite, which indicates the shape-memory property, cannot be achieved.

In one embodiment of the present invention, the nitinol nanofiber may have a metal oxide surface layer.

The metal oxide surface layer may be a crystal structure, an amorphous structure, or a coated oxide film. In addition, the thickness of the metal oxide surface layer may be 10% to 30% of the diameter of the fiber.

The nitinol nanofiber having a metal oxide surface layer has propitious surface cell affinity than a nitinol nanofiber that is not oxidized, thereby being more biocompatible.

In one embodiment of the present invention, the metal oxide surface layer of the nitinol nanofiber contains 10 to 30 at.% of nickel, 10 to 50 at.% of titanium, 25 to 70 at.% of oxygen, and 10 to 35 at.% of one or more elements selected from the group consisting of Mo, Fe, Al, C, and N.

When the content of each component in the alloy composition is outside the range described above, the surface cell affinity and the tissue growth compatibility are reduced, resulting in lower biocompatibility.

In one embodiment of the present invention, a cross-section of the nitinol nanofiber is an irregular saw blade shape, a silkworm cocoon shape, a clover leaf shape, a circular shape, an oval shape, a flat plate shape, a square shape, a triangular shape, or a hollow shape.

With regard to the cross-sectional shape of the nitinol nanofiber, there is no temperature gradient when heated with an IR heater compared to conventional heat treatment rolls used in the wire drawing step. Therefore, the nanofibers may take various cross-sectional shapes. Compared to the shapes of conventional fibers, fibers having various cross-sectional shapes have the advantage of being able to make a fiber bundle that is more compact and has increased density and strength.

In one embodiment of the present invention, the surface of the nitinol nanofiber is coated with one or more polymers selected from the group consisting of polyglycolic acid (PGA), poly-L-lactic acid (PLLA), poly-lact-co-glycolic acid (PLGA), polycaprolactone (PCL), polydioxanone (PDS), poly-L-lactide-co-ε-caprolactone (PLCL), chitosan (CHT), and cellulose nanocrystal (CNC).

When the surface of the nitinol nanofiber is coated with a polymer, a synergy effect of adding biocompatibility to the nitinol nanofiber having a shape memory property, super-elasticity, and resilience can be obtained.

In one embodiment of the present invention, the nitinol nanofiber is a bio-use nitinol nanofiber that is applicable to body parts experiencing repeated flexural motion, repeated stretching and contraction motion, or repeated twisting and restoring motion.

The nitinol nanofiber of the present invention can be used as substitutes for moving body parts, for example, ligaments such as joints or cartilage of animals or humans.

In one embodiment of the present invention, the nitinol nanofiber is a medical nitinol nanofiber that is applicable to body parts experiencing repeated flexural motion, repeated stretching and contraction motion, or repeated twisting and restoring motion.

The nitinol nanofiber of the present invention can be used as medical artificial ligaments for animal or human ligament reconstruction.

In one embodiment of the present invention, a method for preparing nitinol nanofibers is as follows:

melting, by high-frequency vacuum induction, alloy components including 40% to 50% by weight of titanium, 50% to 60% by weight of nickel, and 0% to 10% by weight of one or more elements selected from the group consisting of Mo, Fe, Al, C, N, and O;

hot forging and hot extruding an alloy ingot obtained through the melting;

repeatedly performing cold drawing and interim annealing in a temperature range of 200° C. to 800° C. on the extruded product, using an IR heater, after the hot forging and hot extruding; and preparing a TiNi-based medical alloy by solution treatment at a temperature in a range of 800K to 1300K for 0.5 to 3 hours and then quenching.

More particularly, in the hot drawing, a heat source is an IR heater. The hot drawing involves a cycle of heating to a temperature range of 600° C. to 800° C. and cooling, a cycle of heating to a temperature range of 400° C. to 550° C. and then cooling, or a cycle of heating to a temperature range of 200° C. or less and then cooling.

According to one embodiment of the present invention, the heat treatment and processing may be optimized by infrared preheating technology before the drawing.

According to one embodiment of the present invention, compared to the heat treatment roll used in the drawing of conventional nitinol nanofiber manufacturing technology, the IR heater does not generate a temperature gradient by supplying heat evenly to the inside of the ingot, thereby having the advantages of: reducing defects during processing; solving the problem that fine fibers having a thickness of 0.1 mm or less break during the drawing; and being capable of controlling the latent heat of a martensite transformation process whereby it is possible to draw nanofibers from an austenite ingot having better mechanical properties (elastic resistance, thermal expansion coefficient, electron permeability, elasticity, yield coefficient, etc.) than martensite.

In addition, the use of an infrared heating technique enables a crystalline oxide film which is more biocompatible than an amorphous or coated oxide film.

Thus, the infrared heating technique can make nanofiber processing easier than conventional non-infrared heating techniques, such as heat treatment rolls, can significantly reduce wire breakage during processing by increasing tensile strength, and can improve plasticity of the drawn wire.

In one embodiment of the present invention, the nitinol nanofiber preparation method further involves one to three times of weak reagent (WR, HF:HNO3:H2O=1:3:100) etching or strong reagent (SR, HF:HNO3:H2O=1:3:3) etching for 1 to 5 minutes, after the repeated annealing.

According to one embodiment of the present invention, the reagent etching has an advantage of improving biocompatibility by increasing an average roughness and an area of a roughened region compared to untreated nitinol nanofibers.

The nitinol nanofiber according to the present invention has excellent physical properties. Therefore, the nitinol nanofibers have significantly improved inherent physical properties. Therefore, the nitinol nanofiber according to the present invention can be used in a variety of applications, for example, as biomaterials and medical materials.

ADVANTAGEOUS EFFECTS

The present invention enhances the average surface roughness of nitinol nanofibers through mechanical-chemical treatment to improve biocompatibility and enhances tissue growing to improve bioavailability. Even though the nitinol nanofiber of the present invention has improved tensile strength, elastic modulus, and maximum restorative stress through infrared irradiation so that fatigue fraction does not easily occur easily although the nitinol nanofiber has a constant roughness. The nitinol nanofiber according to the present invention has good biocompatibility because an oxide layer is formed. Another effect of the present invention is to provide bio-use nitinol nanofibers that have bioavailability due to good biocompatibility thereof. Thus, the nitinol nanofibers of the present invention can be used as medical materials.

BEST MODE

Hereinafter, the present invention will be described in detail with reference to examples.

Examples 1 to 3 and Comparative Examples 1 to 4: Preparation of Nitinol Nanofibers The nitinol nanofibers of Examples and Comparative Example were prepared using the same manufacturing method, except for the conditions shown in Table 1.

Raw material powders of titanium (Ti) and nickel (Ni) were dried to remove moisture. This drying minimizes the amount of gas generated during a synthesis reaction.

In the drying step, the powders were dry-mixed in an atomic weight ratio of about 1:1 to produce a powder mixture in which the powders were uniformly mixed.

The powder mixture obtained through the mixing was reacted by hot electromagnetic synthesis in a reactor and then the resulting titanium-nickel product was cooled in a cooling water bath.

Impurities on the surface of the titanium-nickel product cooled through the cooling step were removed to produce a nitinol ingot.

The prepared nitinol ingot was melted, and the resulting molten nitinol was spun into nitinol nanofibers.

In the spinning, the nitinol nanofibers were inserted into an IR LED device (radially arranged 96 IR LEDs ("Kingbright" type L-34R3BY, wavelength 940 nm, output 140 mW)) and heated by LEDs. A wire leading inlet deflects the geometrical axis of the device at each instant. As the outer die performed a continuous circular movement, the contact area between the wire and the wall of the die made the same circular movement. Since the wire performed translation motion, and the die performed circular motion, the contact area moved helically on the surface and covered the entire surface at an appropriate speed. A bending load and a maximum mechanical load were applied to the surface of the wire in the contact area, and the wire was drawn. This process was repeated and annealing was performed at varying temperatures.

After the annealing, the drawn wires were ultrasonically washed with an appropriate cleaning agent for 5 minutes. Next, the wires were subjected to mechanical-chemical etching processing in which chemical etching was performed with a weak reagent (WR) (HF:HNO3:H2O=1:3:100) or a strong reagent (SR) (HF:HNO3:H2O=1:3:3) at room temperature, and mechanical polishing was then performed. Thus, finally, nitinol nanofibers were obtained.

TABLE 1

| | Heating Method | Mechanical-Chemical Processing | Final Diameter |
|---|---|---|---|
| Example 1 | IR LED | 2 times of WR etching (1.5 um, 0.8 um) for 12 hours each time | 0.8 um |
| Example 2 | IR LED | 12-hour single WR etching | 0.8 um |
| Example 3 | IR LED | 1-minute single SR etching | 0.8 um |
| Example 4 | IR LED | x | 0.8 um |
| Comparative Example 1 | Heat treatment rolls | x | 100 um |
| Comparative Example 2 | IR LED | 4 times of WR etching (10 um, 5 um, 1.5 um, 0.8 um) for 12 hours each time | 0.8 um |
| Comparative Example 3 | IR LED | 6-minute single SR etching | 0.8 um |

[Equipment used to measure surface condition and microstructure]

1) Measurement of surface condition and microstructure: Philips SEM 515, Quanta 3D microscope, acceleration voltage of 20 to 30 kV, and beam size of 5 to 20 nm 2) Energy dispersive X-ray microanalysis: EDAX ECON IV deteror.

Experimental Example 1: Measuring fiber diameter according to heating method

After dropping a drop of water in the center of a slide glass and laying two or three strands of each of the prepared nitinol fibers, the strands of nitinol nanofiber were covered by a cover glass, and the diameter of each strand was measured using a microscope.

As can be seen from Table 1, in the case of Comparative Example 1 in which a conventional heat treatment method is used instead of the IR LED heating, nitinol fiber with the final diameter of 1 mm can be manufactured. When the diameter was smaller than 1 mm, the fibers broke, and the function of the fibers was lost.

Experimental Example 2: Measurement of surface roughness

The surface roughness was measured using a Hommel tester T1000 using an ISO 11562 (M1) filter and quantified using DIN/ISO standards.

TABLE 2

| | Comparative Example 1 | Example 1 | Example 2 | Comparative Example 3 | Example 3 | Comparative Example 4 | Example 4 |
|---|---|---|---|---|---|---|---|
| Roughened Area (8) | 6 | 24 | 16.4 | 30.5 | 13.5 | 28.1 | 26.8 |
| Average roughness (nm) | 0.45 ± 0.03 (um) | 1.75 ± 0.24 | 2.40 ± 0.41 | 0.82 ± 0.05 | 9.7 ± 1.2 | 15.16 ± 1.4 | 1.32 ± 0.13 |
| Height difference (nm) between top and | 3.85 ± 1.24 (um) | 15.1 ± 1.67 | 24.1 ± 1.34 | 8.4 ± 1.89 | 43.8 ± 0.65 | 82.6 ± 1.65 | 12.5 ± 1.05 |

TABLE 2-continued

| | Comparative Example 1 | Example 1 | Example 2 | Comparative Example 3 | Example 3 | Comparative Example 4 | Example 4 |
|---|---|---|---|---|---|---|---|
| bottom | | | | | | | |
| Cell adhesion | + | ++ | ++ | + | +++ | ++ | ++ |
| Tissue growth | + | + | ++ | + | +++ | + | + |

Regarding Example 4, a crystalline oxide film was formed by IR irradiation through which Ni and Ti moved, without etching. In such a condition, the roughness was measured.

Experimental Example 3: Oxide profile measurement test

The full-width at half-maximum method was used for measurement.

TABLE 3

| | | Comparative Example 1 | Example 1 | Example 2 | Example 3 | Example 4 |
|---|---|---|---|---|---|---|
| Composition of metal oxide surface layer (at. %) | Ti | 36.4 | 24.3 | 26 | 27.8 | 30.09 |
| | Ni | 34.3 | 14.4 | 19.5 | 20.6 | 13.73 |
| | O | 23.88 | 47.1 | 42.2 | 51.6 | 56.18 |
| | N | 0 | 3.7 | 4.2 | 0 | 0 |
| | C | 0 | 10.5 | 8.1 | 0 | 0 |

Experimental Example 4: Measurement of elastic modulus, maximum recovery stress, and tensile strength Measurements were made at room temperature using a conventional screw-driven testing machine, Instron-4206. The strain rate was $10^{-3} s^{-1}$, and the load was applied continuously until the sample reached the breaking point.

TABLE 4

| | Example 1 | Example 2 | Example 3 | Example 4 | Comparative Example 1 | Comparative Example 3 |
|---|---|---|---|---|---|---|
| Elastic modulus (GPa) | 114 | 120 | 85 | 57 | 28 | 97 |
| Maximum tensile strength (MPa) | 1650 | 1770 | 1615 | 1277 | 482 | 1384 |
| Maximum recovery stress (MPa) | 760 | 786 | 735 | 654 | 381 | 724 |

In the case of Comparative Example 4, the degree of etching was high, but due to the weakening of the strength, it was difficult to measure the physical properties because a break occurred during etching. The nitinol nanofibers of the present invention do not have a foreign body reaction with living tissue, can exist in the human body for an increased period of time due to improved maximum tensile strength and elastic modulus, and have fatigue properties, corrosion properties, and shape memory properties such as superelasticity. Therefore, nitinol nanofibers of the present invention have mechanical, physical, and chemical properties suitable for use in bio-use and medical applications.

While the present invention has been described in detail centering on the characteristic parts, those skilled in the art will appreciate that the specific description is only about preferred embodiments and does not limit the scope of the present invention. Accordingly, the scope of the present invention should be defined by the claims appended hereto and their equivalents.

The invention claimed is:

1. A nitinol nanofiber made of an alloy of nickel and titanium, wherein the nitinol nanofiber has a nanofiber shape having a largest diameter in a range of 10 nm to 1,000, has a surface roughness formed over an area of 10% to 30% of the entire surface of the nitinol nanofiber, has an average roughness in a range of 0.5 nm to 40 nm, and has a roughness-formed region in which a height difference between top and bottom is in a range of 0.01 to 80 nm,
    wherein the nitinol nanofiber comprises a metal oxide surface layer on a surface thereof, and
    wherein the metal oxide surface layer contains 10 to 30 at.% of nickel, 10 to 50 at.% of titanium, 25 to 70 at.% of oxygen, and a total of 10 to 35 at.% of one or more elements selected from the group consisting of Mo, Fe, Al, C, and N.

2. The nitinol nanofiber according to claim 1, further having one or more properties selected from among a density of 4 to 9 g/cm$^3$, an elastic modulus of 20 to 120 GPa, a maximum recovery rate of 100%/1 million cycles, a maximum recovery stress of 800 MPa, and a thermal expansion modulus of $6.6 \times 10^{-6}$ to $11 \times 10^{-6}$/° C.

3. The nitinol nanofiber according to claim 1, wherein the nitinol nanofiber has a maximum tensile strength in a range of 1000 MPa to 2000 MPa.

4. The nitinol nanofiber according to claim 1, wherein the cross-sectional shape of the nitinol nanofibers has an irregular saw blade shape, a silkworm cocoon shape, a clover leaf shape, a circular shape, an oval shape, a flat plate shape, a square shape, a triangular shape, or a hollow shape.

5. The nitinol nanofiber according to claim 1, wherein the surface of the nitinol nanofiber is coated with one or more polymers selected from the group consisting of polyglycolic acid (PGA), poly-L-lactic acid (PLLA), poly-lact-co-glycolic acid (PLGA), polycaprolactone (PCL), polydioxanone (PDS), poly-L-lactide-co-ε-caprolactone (PLCL), chitosan (CHT), and cellulose nanocrystal (CNC).

6. The nitinol nanofiber according to claim 1, wherein the nitinol nanofiber is a bio-use nitinol nanofiber applicable to a body part experiencing repeated flexural motion, repeated stretching and contraction motion, or repeated twisting and restoring motion.

7. The nitinol nanofiber according to claim 1, wherein the nitinol nanofiber is a medical nitinol nanofiber applicable to body parts experiencing repeated flexural motion, stretching and contraction motion, or repeated twisting and restoring motion.

8. The nitinol nanofiber according to claim 1, wherein the nitinol nanofiber is a medical nitinol nanofiber applied to an artificial ligament.

9. A method of manufacturing a nitinol nanofiber according to claim 1, the method comprising: melting, by high-frequency vacuum induction, alloy components comprising 40% to 50% by weight of titanium, 50% to 60% by weight of nickel, and 0% to 10% by weight of one or more elements selected from the group consisting of Mo, Fe, Al, C, and N; hot forging and hot extruding an alloy ingot obtained through the melting; repeating drawing and interim annealing in a temperature range of 200° C. to 800° C. using an IR heater, after the hot forging and hot extruding; and performing solution treatment in a temperature range of 800 K to 1300 K for 0.5 to 3 hours and then quenching to produce a TiNi-based medical alloy.

10. The method according to claim 9, further comprising one to three times of WR etching or one to five minutes of SR etching after the repeating of the annealing.

\* \* \* \* \*